United States Patent [19]

Jung et al.

[11] Patent Number: 5,399,740
[45] Date of Patent: Mar. 21, 1995

[54] TRIS(SILYL)METHANES AND THEIR PREPARATION METHODS

[75] Inventors: Il N. Jung, Seoul; Seung H. Yeon, Kyungki-Do; Joon S. Han, Seoul, all of Rep. of Korea

[73] Assignee: Korea Institute of Science and Technology, Seoul, Rep. of Korea

[21] Appl. No.: 164,944

[22] Filed: Dec. 10, 1993

[51] Int. Cl.$^6$ ............................................. C07F 7/08
[52] U.S. Cl. ................................................... 556/435
[58] Field of Search ...................................... 556/435

[56] References Cited

U.S. PATENT DOCUMENTS

| | | |
|---|---|---|
| 4,788,312 | 11/1988 | Paciorek et al. ............ 556/435 |
| 5,026,893 | 6/1991 | Paciorek et al. ............ 556/435 |
| 5,075,477 | 12/1991 | Jung et al. . |
| 5,233,069 | 8/1993 | Jung et al. . |
| 5,235,083 | 8/1993 | Jung et al. . |

OTHER PUBLICATIONS

"Organosilicon Halides," E. G. Rochow, U.S. Pat. No. 2,380,995 (1945) C.A. 39, 4889 (1945).
"The Direct Synthesis of Organosilicon Compounds," E. G. Rochow, J. Amer. Chem. Soc., 67, 963 (1945).
"Catalyst Based on Copper Used . . . Methylchlorosilanes," P. Trambouze et al. J. Chem. Phys. 51, 505 (1954).
"Inorganic Syntheses, vol. III" by E. G. Rochow, McGraw-Hill, New York, 1950, p. 56.
"Synthesis of Organosilicon Compounds. III," A. L. Klebanskii et al., Zhr. Obschei Khim., 27, 2648 (1957), C.A. 52, 7131d.
R. J. H. Voorhoeve et al., "Organohalosilanes Precursors to Silicones," Elsevier Pub. Co., pp. 139-147, 1964.
"Organosilicon Compounds," J. E. Sellers et al., U.S. Pat. No. 2,449,821 (1948); C.A. 43, 1051b (1949).
"Alkylhalosilanes," B. A. Bluestein, U.S. Pat. No. 2,887,502 (1959); C.A. 53, 18865c (1959).
"Direct Synthesis of Alkylpolysilane Chlorides," Petrov et al. Zh. Obshch. Khim., 26, 1248 (1956); C.A., 51, 6505f (1957).
"Entstehung von Trichlorsilyl-trichlor-athen . . . Gemischen," Muller et al., Chem. Ber., 92, 1957 (1959).
"Die Umsetzung von Bis-trichlorsilyl-chlormethan mit Silicium," Muller et al., Chem. Ber., 96, 2894 (1963).

*Primary Examiner*—Paul F. Shaver
*Attorney, Agent, or Firm*—Birch, Stewart, Kolasch & Birch

[57] ABSTRACT

The present invention relates to a process for preparing tris(silyl)methanes by directly reacting a mixture of α-dichloromethylsilanes represented in formula I and hydrogen chloride or alkyl chlorides represented in formula II, with silicon metal to give the tris(silyl)methanes having two dichlorosily groups (formula III), the tris(silyl)methanes having one trichlorosilyl group and one dichlorosilyl group (formula IV), and the tris(silyl)metranes having two trichlorosilyl groups (formula V) in moderately high yields in the presence of copper catalyst at a temperature from 250° C. to 350° C.

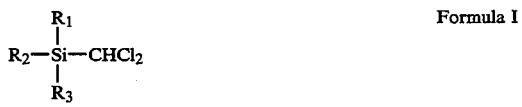

Formula I

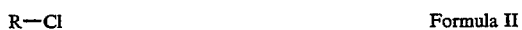

Formula II

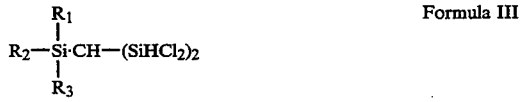

Formula III

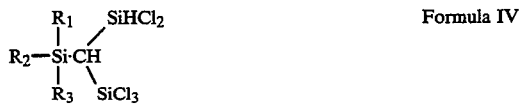

Formula IV

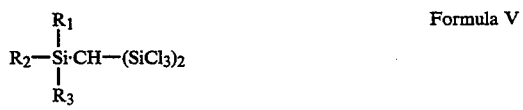

Formula V

Wherein R represents hydrogen, alkyl($C_1$-$C_4$), or $CH_2CH_2Cl$, and $R_1$, $R_2$, and $R_3$ represent independently hydrogen or chloride.

1 Claim, No Drawings

TRIS(SILYL)METHANES AND THEIR PREPARATION METHODS

BACKGROUND OF THE INVENTION

1. Field of the Invention

The present invention relates to a process for preparing tris(silyl)methanes by directly reacting a mixture of α-dichloromethylsilanes represented by formula I and hydrogen chloride or alkyl chlorides represented by formula II, with silicon metal to give the tris(silyl)methanes having two dichlorosilyl groups (formula III) and the tris(silyl)methanes having one trichlorosilyl group and one dichlorosilyl group (formula IV) in moderately high yields in the presence of copper catalyst at a temperature from 250° C. to 350° C. A different major product is obtained depending upon the alkyl chloride incorporated. For example, n-butyl chloride, t-butyl chloride, and propyl chloride gave tris(silyl)methanes with one hydrogen substituted on each of the two silicon atoms as the major product. When 1,2-dichloroethane is incorporated, tris(silyl)methanes having two trichlorosilyl group is the only major product. The preferred reaction temperature range is 300°-330° C. Useful copper catalysts include copper metal, copper salts, partially oxidized copper.

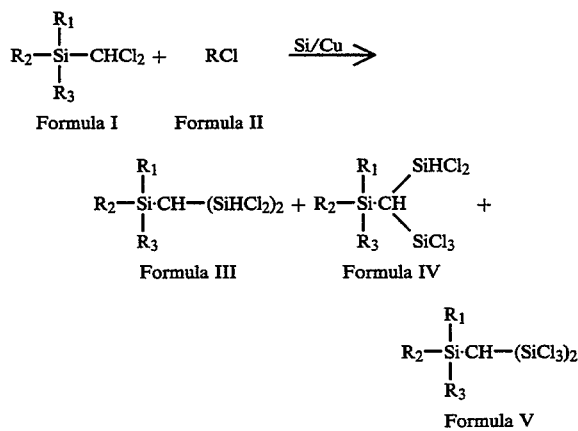

In the formulas, R represents hydrogen, alkyl($C_1$-$C_4$), or $CH_2CH_2Cl$, and $R_1$, $R_2$ and $R_3$ represent independently hydrogen or chloride.

2. Description of the Prior Art

Methylchlorosilanes are the most important starting materials for silicons. E. G. Rochow discovered the direct process for the synthesis of methylchlorosilanes, reacting elemental silicon with methylchloride in the presence of a catalyst in 1940 (E. G. Rochow U.S. Pat. No. 2,380,995).

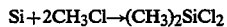

$$Si + 2CH_3Cl \rightarrow (CH_3)_2SiCl_2$$

The reaction gives dimethyldichlorosilane, methyltrichlorosilane, trimethylchlorosilane, and tetrachlorosilane. A number of high boiling compounds are also found in the mixture of the products in a small quantity. The reaction rate and the nature of products depend on a large number of factors. These determining factors include the nature of starting materials, catalyst, reaction temperature, reaction pressure, the type of reactor used, and the degree of conversion of silicon and methyl chloride.

The catalyst for the direct process is always copper, in some cases co-catalysts such as zinc, aluminum, cadmium, etc. are added. The co-catalysts enhance the reactivity of silicon metal and shorten the induction period and increase the selectivity of dimethyldichlorosilane production. The reaction is carried out at 250°-350° C., and the yield of dimethyldichlorosilane decrease at temperatures above 300° C. In the absence of a catalyst, the reaction is sluggish and gives irreproducible results (E. G. Rochow, J. Am. Chem. Soc., 67, 963 (1945)). The composition of products depends on the amount of copper used. The greater amount of copper is used, the higher is the chlorine content of the resulting products. The greatest catalytic efficiency is obtained when the amount of copper is 10% of the amounts of silicon.

The reactivity of the silicon-copper mixture is connected with the formation of an intermetallic η-phase ($Cu_3Si$). The presence of the η-phase in the mixture is of fundamental importance for the seletive synthesis of dimethyldichlorosilane. It is known that the mixture of silicon powder and copper powder is heated 800° C. to 1000° C. in nitrogen, or better in hydrogen, the powders become sintered and the η-phase in formed (P. Trambouze and B. Imelik, J. Chem. Phys. 51, 505 (1954)). The η-phase is also chemically prepared by heating cuprous chloride with silicon at a temperature above 350° C. (E. G. Rochow in Inorganic synthesis, III, McGraw-Hill, New York 1950, p56)

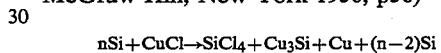

$$nSi + CuCl \rightarrow SiCl_4 + Cu_3Si + Cu + (n-2)Si$$

The reaction rate and the composition of the products in the direct process are highly temperature-dependent (A. L. Klebamskii and V. S. Fikhtengolts, J. Gen. Chem. U.S.S.R., 27, 2693 (1957)). It is very important to maintain the reaction temperature at an accurately specified temperature and to prevent and hot spot developing in the agglomerates of the solid phase. It is reported that at higher temperatures, the deposition of carbon on the surface of the metal mixture occur which slows down the reaction (J. C. Vlugter, and R. J. H. Voorhoeve, Conf. Accad. Lin-cei, Alta Tech. Chim. 1961 p81(1962)). This is why the reactor for the direct synthesis of methylchlorosilane must have a high thermal stability and an efficient heat transfer.

The direct process can be carried out in fixed bed, in strired bed, and also in fluidized bed reactors. The process with the stirred bed reactors has the advantages over the fixed bed operation that the heat of reaction can be removed more easily and the movement of the powders causes fresh surface to be continuously exposed. Sellers and Davis reported that a mechanically stirred fluidized bed could be used (J. E. Sellers and J. L. Davis, U.S. Pat. No. 2,449,821). The metal powder was agitated in an up and down motion in a vertical reactor by means of spiral band rotated by a central shaft while a stream of methyl chloride was moved up-ward through it. Bluestrim used a fluidized bed reactor for the production of methylchlorosilane (B. A. Bluestrim, U.S. Pat. No. 2,887,502).

Petrov et al reported the preparation of chlorosilaalkanes by reacting silicon metal with α-dichloromethylsilanes. The reaction of α-dichloromethylsilanes with silicon metal at 360° C. gave 14% yield of tris(trichlorosilyl)methane and about 70% by-products due to the decomposition of the starting material (A. D. Petrov, S. I. Sahykh-Zade, E. A. Chernyshev. V. F. Mironov, Zh. Obschch. Khim., 26 1248 (1956)). The expected tetrakis(silyl)methane was not obtained when bis (trichlorosilyl)dichloromethane was reacted with metallic silicon. All the products obtained were from the secondary reaction between metallic silicon and the compounds produced from the decomposition of bis(trichlorosilyl) dichloromethane. Several year later, Muller and his co-workers also studied the same reaction and reported that tetrakis (silyl)methane was not produced but the starting material decomposed (R. Muller and H. Beyer, Chem. Ber., 92, 1957 (1959); 96, 2894 (1963)).

We reported that trisilalkanes as the major products and bis(silyl)methanes as the minor products were prepared by reacting α-chloromethylsilanes with metallic silicon in the presence of copper catalyst at a temperature from 250° C. to 350° C. The copper catalyst was used in an amount of the 1-20% of total contact mixture, but the preferred amount was 5-10%. The reaction could be carried out in a fluidized bed or in a stirred bed reactor. Addition of microspherical acid clay to silicon metal improved the fluidization and gave better results (I. N. Jung, G. H. Lee, S. H. Yeon, M. Suk, U.S. Pat. No. 5,075,477 (1991. 12. 24)).

The reaction can be illustrated as follows:

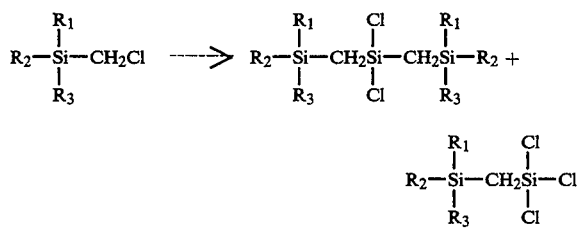

wherein $R_1$, $R_2$, $R_3$ may independantly be chloride or methyl.

We also reported the direct synthesis of Si—H containing bis(silyl)methanes by reacting silicon metal with a mixture of α-chloromethylsilanes and hydrogen chloride. The bis(silyl)methane containing dichlorosilyl group was obtained as the major product and bis(silyl)methane containing trichlorosilyl group was obtained as the minor product. The major product could be explained by the reaction of the same silicon atom with each mole of two starting materials. The results suggest that the reactivities of the two starting materials were not much different. The major portion of the other by-products was trichlorosilane and tetrachlorosilane which were produced from the reaction between silicon metal and hydrogen chloride. The same results were obtained when hydrogen chloride was substituted by alkyl chlorides such as 1,2-dichloroethane, propyl chloride, n-butyl chloride or t-butyl chloride, because alkyl chlorides decomposed to give off hydrogen chloride (Korean Patent Application No. 91-24243).

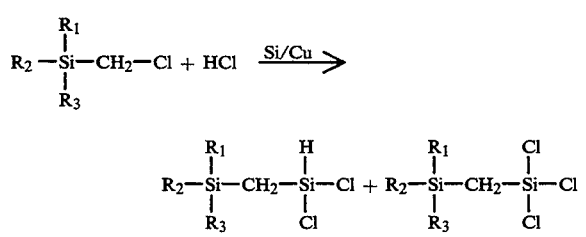

wherein $R_1$, $R_2$, $R_3$ may independently be chloride or methyl.

We also found that bis(silyl)methanes having two dichlorosilyl groups at the both ends of the molecule along with bis(silyl)methane having two trichlorosilyl groups at the both ends and bis(silyl)methane having one dichlosilyl group and one trichlorosilyl group at each end were obtained by reacting a mixture of methylene chloride and hydrogen chloride (Korean Patent Application No. 92-935).

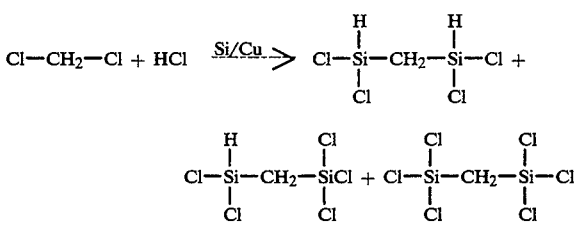

SUMMARY OF THE INVENTION

The present invention relates to a process for preparing tris(silyl)methanes by directly reacting a mixture of α-dichloromethylsilanes represented by formula I and hydrogen chloride or alkylchloride represented by formula II, with metallic silicon to give the tris(silyl)methanes having two dichlorosilyl groups (formula III) and the tris(silyl)methanes having one trichlorosilyl group and one dichlorosilyl group (formula IV) in moderately high yields in the presence of copper catalyst at a temperature from 250° C. to 350° C. A different major product is obtained depending upon the alkyl chloride incorporated. For example, n-Butyl chloride, t-butyl chloride, and propyl chloride gave tris(silyl)methanes with one hydrogen substituted on each of the two silicon atoms as the major product. When 1,2-dichloroethane is incorporated, tris(silyl)methanes having two trichlorosilyl group is the only major product. The preferred reaction temperature range is 300°-330° C. Useful copper catalysts include copper metal, copper salts and partially oxidized copper.

The reaction can be illustrated as follows:

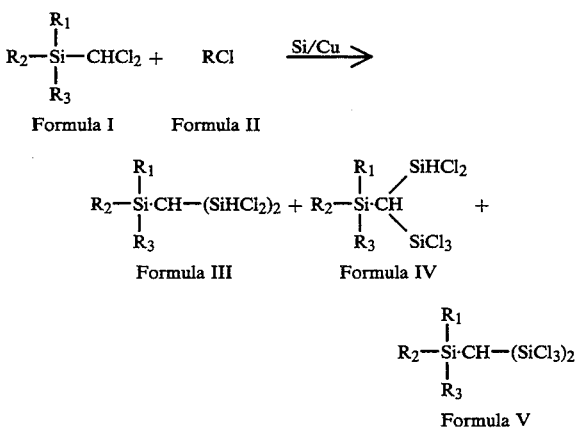

wherein R represents hydrogen, alkyl($C_1$-$C_4$), or $CH_2CH_2Cl$, and $R_1$, $R_2$, and $R_3$ represent independently hydrogen or chloride.

The α-dichloromethylsilanes represented by formula I may be blended with hydrogen chloride or alkyl chloride of formula II before they are introduced to the reactor. They can be mixed in gaseous state after they are vaporized or in liquid state when the formula II compound is a liquid. Although the formula I compound may be mixed with the formula II compound in all proportions by weight or by volume, the actual amount the formula II used will depend upon the desired ratio of hydrocarbon groups to chlorine atoms in the product. Thus, formula II may be advantageously used from about 0.1 to 6 moles per mole of formula I employed, the preferred ratio is 3 to 5 moles.

The reaction can be carried out in a fluid bed or in a stirred bed reactor. In the fluidized bed reaction, the addition of inert nitrogen gas to the starting gases is recommended to improve the fluidization. This also helps to remove the high boiling products out of the reactor. Metallurgical grade silicon is employed in the process of this invention, which contained more than 95% silicon by weight. The preferred purity of silicon is higher than 98%. The particle size of the silicon is 1–200 micron, but 20–200 micron is used for the fluidized reaction. The reaction temperature is from 200° C. to 360° C. The preferred reaction temperature range is 260°–320° C. The pressure at which the reaction of present invention is conducted is not critical and may be varied from 1 to 5 atmospheres, preferably 1 to 3 atmospheres. Addition of micro-spherical acid clay to silicon metal improves the fluidization and give better results.

The commercially available copper catalysts for the reaction between silicon and methyl chloride are also found to be good catalysts for these reactions. The content of copper catalyst is 1–20% of the total contact mass. The preferred copper content is 5–10%. The process in this invention may include using promoters. The range of the promoters content is 0.001–2.0%. The promoters include calcium, barium, zinc, tin, cadmium, manganese, magnesium, silver, and chromium, but are not limited to them.

The invention will be further illustrated by the following examples. It is, however, not intended that this invention will be limited by the examples.

EXAMPLE 1

Preparation of Si/Cu Contact Mixture (I)

After about 360 g (100–325 mesh) of silicon was mixed with 62.3 g of CuCl (10% of copper based on the weight of the silicon and copper) as a catalyst in order to provide a mixture, the mixture was contained in the reactor. Thereafter, the mixture was heated to a temperature 250° C. At this time, the agitator rotated at 60 rpm, in order to mix the mixture completely together with blowing slowly dried nitrogen. When the temperature in the relactor is raised to about 370° C., the silicon reacts with the CuCl to form η-phase $Cu_3Si$, and $SiCl_4$ is obtained as a by-product which is removed from the reactor. In the case of using a promoter, 0.8 g of a promoter metal is added to the mixture after the reaction is completed.

EXAMPLE 2

Preparation of Si/Cu Contact Mixture (I-2–I-15)

In case of using metallic copper or copper catalysts which were used in the synthesis of methylchlorosilanes instead of the CuCl as described in Example 1, silicon was mixed with 10% of the copper based on the weight of the silicon. The mixture was heated at 350° C. for 2 hours in the reactor together with blowing hydrogen chloride or methyl chloride in order to be activated.

The compositions of the contact mixtures prepared in Example 1 and 2 are shown in Table 1.

TABLE 1

| | | Compositions of Si/Cu Contact Mixture | | | | | | |
|---|---|---|---|---|---|---|---|---|
| | | Cu Catalyst | | | | Promoter | | |
| Sample No. | Si (g) | Form | (g) | Metal | (g) | Metal | (g) | Remark |
| I-1 | 360 | CuCl | 62.3 | | | | | |
| I-2 | 380 | Cu | 20.0 | | | | | |
| I-3 | 360 | Cu | 40.0 | Cd | 2.0 | | | |
| I-4 | 360 | Cu | 40.0 | Zn | 2.0 | | | |
| I-5 | 380 | Cu | 20.0 | Cd | 2.0 | Sn | 0.02 | |
| I-6 | 380 | Cu | 20.0 | Ca | 2.0 | | | |
| I-7 | 380 | Cu | 20.0 | Ca | 2.0 | Cd | 2.0 | |
| I-8 | 360 | Cu | 40.0 | Ag | 2.0 | | | |
| I-9 | 360 | Cu | 40.0 | Aa | 2.0 | Cd | 2.0 | |
| I-10 | 360 | Cu | 40.0 | Mn | 2.0 | | | |
| I-11 | 360 | Cu | 40.0 | Mn | 2.0 | Cd | 2.0 | Acid clay added |
| I-12 | 360 | Cu | 40.0 | Mg | 2.0 | | | |
| I-13 | 360 | Cu | 40.0 | Mg | 2.0 | Cd | 2.0 | |
| I-14 | 360 | Cu | 40.0 | Cr | 2.0 | | | Acid clay added |
| I-15 | 360 | Cu | 40.0 | Cr | 2.0 | Cd 2.0 | | |

EXAMPLE 3

Reaction of Silicon with 1:4 Mixture of Dichloromethyldimethylchlorosilane and Hydrogen Chloride 402 g of Si/Cu contact mixture(I-3) prepare in Example 2 was charged in an agitating-type reaction bath, and dry nitrogen gas was blown into the reactor at the rate of 200 ml/min. After increasing the temperature in the reactor up to 300° C., dichloromethyldimethylchlorosilane was pumped using a syringe pump at the rate of 20.0 ml/hr to the evaporator attached to the bottom of the reactor, while hydrogen chloride were also blown therein at the rate of 200 ml/min. 1 minute after the initiation of pumping, increase of the temperature caused by an exothermic nature of the reaction was observed and reaction products being to flow along the wall of an receiver flask. While maintaining the above conditions, reaction product was taken every half and hour.

The obtained reaction products were analyzed by using a gas chromatograph (packed column, 5% SE-54, 0.9 m×⅛" OD. SS., TCD) and fractionally distilled to separate its constituents from one another, so that their structures could be determined. The structures of each constituent was determined by using a nuclear magnetic resonance spectroscopy and a mass spectrometry. After the reaction for 2 hours, 78.6 g of products was collected, while 49.5 g of dichloromethyldimethylchlorosilane was used.

The composition of the products contained 43.3 g (55.1%) of 1,1,3-trichloro-3-methyl-2-(dichlorosilyl)-1,3-disilabutane (Formula III); [NMR (CDCl$_3$), δ, 5.81 (d, 2H, Si-13 H), 1.24 (s, 1H, —CH=), 0.75 (s, 6H, —CH$_3$)] and 14.5 g (18.5%) of 1,1,3-trichloro-3-methyl-2-(trichlorosilyl)-1,3-disilabutane (Formula IV); [NMR(CDCl$_3$); δ, 5.85 (s, 1H, Si—H), 1.53 (s, 1H, —CH=), 0.79 (s, 6H, —CH$_3$)] and 1.4 g (1.8%) of 1,1,1,3-tetrachloro-3-methyl-2-(trichlorosilyl)-1,3-disilabutane (Formula V); [NMR(CDCl$_3$), δ, 1.74 (s, 1H, —CH=), 0.83 (s, 6H, —CH$_3$)]. 26.4% of by-products contained 1,1,3-trichloro-3-methyl-1,3-disilabutane (10.7%) and 1,1,1,3-tetrachloro-3-methyl-1,3-disilabutane (1.2%), trichlorosilane (5.7%), tetrachlorosilane (0.8%), trimethylchlorosilane (1.0%), and 7.0% was unidentified substances.

The reaction was carried out under the same condition and by the same reactor as employed above, except that the reaction temperature varied from 240° C. to 340° C. The results obtained from the reactions are shown in Table 2.

TABLE 2

Reaction Temperatures and Products composition

| Entry No. | Temp. (°C.) | Silane Amt. (g) | React. Time (hr) | Products Amt. (g) | Composition of Product (%) | | | |
|---|---|---|---|---|---|---|---|---|
| | | | | | III | IV | V | others |
| 1 | 240 | 49.5 | 2.0 | 79.3 | 57.2 | 14.4 | 1.1 | 27.3 |
| 2 | 260 | 49.5 | 2.0 | 79.3 | 57.7 | 16.6 | 1.5 | 24.2 |
| 3 | 280 | 49.5 | 2.0 | 78.6 | 55.1 | 18.5 | 1.8 | 24.6 |
| 4 | 300 | 49.5 | 2.0 | 77.0 | 54.0 | 21.7 | 2.5 | 21.8 |
| 5 | 320 | 49.5 | 2.0 | 76.2 | 53.3 | 21.6 | 2.2 | 22.9 |
| 6 | 340 | 49.5 | 2.0 | 73.2 | 47.5 | 23.4 | 4.3 | 24.8 |

EXAMPLE 4

Reaction of Silicon with a Mixture of Dichloromethyldimethylchlorosilane and Hydrogen Chloride The reaction was carried out 320° C. under the same condition and by the same reactor as employed in Example 3, except that the mixing ratio of dichloromethyldimethylchlorosilane and hydrogen chloride varied from 1:2 to 1:6. The results obtained from the reactions are shown in Table 3. The results shown in Entry No. 10 of Table 3 are obtained from the reaction in which 20.0 g (5% based on the weight of the silicon and copper) of acid clay was added to the contact mixture. The contact mixture was recharged after 20% conversion and results were about same.

TABLE 3

The mixing ratio of Reactants and Product Compositions

| Entry No. | Silane: HCl | Silane Amt. (g) | React. Time (hr) | Products Amt. (g) | Composition of Product (%) | | | | Remark |
|---|---|---|---|---|---|---|---|---|---|
| | | | | | III | IV | V | others | |
| 7 | 1:2 | 49.5 | 2.0 | 68.2 | 43.3 | 28.5 | 4.3 | 23.9 | |
| 8 | 1:3 | 49.5 | 2.0 | 72.2 | 51.0 | 27.2 | 5.5 | 16.3 | |
| 5 | 1:4 | 49.5 | 2.0 | 76.2 | 53.3 | 21.6 | 2.2 | 22.7 | |
| 9 | 1:6 | 49.5 | 2.0 | 86.0 | 47.9 | 16.9 | 2.0 | 33.2 | |
| 10 | 1:4 | 49.5 | 2.0 | 77.3 | 53.5 | 21.4 | 2.2 | 22.9 | acid clay |

EXAMPLE 5

Reaction of Silicon with a Mixture of Dichloromethyldimethylchlorosilane and Hydrogen Chloride The reaction was carried out under the same condition and by the same reactor as employed in Exp. No. 3 of Example 3, except the different contact mixture was used. All the contact mixture listed in Table 1 have been tested and the results obtained from the reactions are shown in Table 4.

TABLE 4

Contact Mixtures and Product Compositions

| Entry No. | contact mixture | Silane Amt. (g) | React. Time (hr) | Products Amt. (g) | Composition of Product (%) | | | | Remark |
|---|---|---|---|---|---|---|---|---|---|
| | | | | | III | IV | V | others | |
| 11 | I-1 | 49.5 | 2.0 | 60.4 | 13.2 | 26.7 | 17.5 | 42.6 | |
| 12 | I-2 | 49.5 | 2.0 | 52.2 | 20.6 | 35.0 | 16.3 | 29.6 | |
| 13 | I-4 | 49.5 | 2.0 | 66.6 | 26.9 | 29.2 | 9.4 | 34.5 | |
| 14 | I-5 | 49.5 | 2.0 | 61.2 | 18.6 | 28.3 | 19.7 | 33.4 | |
| 15 | I-6 | 49.5 | 2.0 | 71.2 | 9.3 | 33.7 | 18.8 | 38.2 | |
| 16 | I-7 | 49.5 | 2.0 | 71.9 | 13.9 | 35.7 | 13.2 | 37.2 | |
| 17 | I-8 | 49.5 | 2.0 | 72.8 | 14.2 | 35.9 | 20.1 | 29.8 | |
| 18 | I-9 | 49.5 | 2.0 | 70.8 | 37.2 | 21.7 | 9.8 | 35.8 | |
| 19 | I-10 | 49.5 | 2.0 | 72.5 | 16.2 | 38.7 | 19.3 | 25.8 | |
| 20 | I-11 | 49.5 | 2.0 | 71.0 | 38.4 | 23.1 | 9.9 | 28.6 | |
| 21 | I-12 | 49.5 | 2.0 | 72.6 | 14.3 | 32.2 | 17.2 | 36.3 | |
| 23 | I-13 | 49.5 | 2.0 | 71.5 | 33.7 | 19.4 | 7.3 | 39.6 | |
| 24 | I-14 | 49.5 | 2.0 | 71.7 | 13.8 | 30.7 | 21.7 | 33.8 | |

TABLE 4-continued

| | | Contact Mixtures and Product Compositions | | | | | | | |
|---|---|---|---|---|---|---|---|---|---|
| Entry No. | contact mixture | Silane Amt. (g) | React. Time (hr) | Products Amt. (g) | Composition of Product (%) | | | | Remark |
| | | | | | III | IV | V | others | |
| 25 | I-15 | 49.5 | 2.0 | 72.1 | 39.2 | 24.2 | 8.7 | 27.9 | |

EXAMPLE 6

Reaction of Silicon with a Mixture of Dichloromethyldimethylchlorosilane and Alkyl Chloride The following experiment demonstrates Exp. No. 26 of Table 5. The reaction was carried out at 280° C. under the same condition and by the same reactor as employed in Example 3, except that the same amount of t-butyl chloride was used as the hydrogen chloride source. 1:4 mixture of dichloromethyldimethylchlorosilane and t-butyl chloride was prepared by mixing 66.6 g (0.375 mole) of dichloromethyldimethylchlorosilane and 138.7 g (1.500 mole) of t-butyl chloride. The mixture was pumped at the rate of 74 ml/hr to the evaporator attached to the bottom of the reactor, while $N_2$ was also blown therein at the rate of 200 ml/min. After the reaction for 2 hours, 83.8 g of products was collected.

The composition of the products contained 36.2 g (43.2%) of 1,1,3-trichloro-3-methyl-2-(dichlorosilyl)-1,3-disilabutane (Formula III), 9.1 g (10.8%) of 1,1,3-chloro-3-methyl-2-(trichlorosilyl)-1,3-disilabutane (Formula IV), and 1.8 g (2.1%) of 1,1,1,3-tetrachloro-3-methyl-2-(trichlorosilyl)-1,3-disilabutane (Formula V). The by-product contained 9.8% of 1,1,3-trichloro-3-methyl-1,3-disilabutane, 2.1% of 1,1,1,3-tetrachloro-3-methyl-1,3-disilabutane. 6.3% of trichlorosilane, and 0.8% of tetrachlorosilane. No starting material was recovered.

The reaction was carried out under the same condition and by the same reactor as employed above, except that the different mixing and different kind of alkyl chloride were used. The gaseous by-product which was not trapped in the condenser was detected to be mostly isobutene produced from the decomposition of t-butyl chloride. n-Butyl chloride, i-propyl chloride, or 1,2-dichloroethane was used instead of t-butyl chloride. In these cases, the gaseous by-product from the decomposition of alkyl chloride was 2-butene, propylene, or ethylene respectively. When the half of the alkyl chloride was replaced by hydrogen chloride, the composition of the reaction products was about same as before. The results obtained from the reactions are shown in Table 5.

TABLE 5

| | | Reaction Conditions and Product Compositions | | | | | | | |
|---|---|---|---|---|---|---|---|---|---|
| Entry No. | RCl | silane: RCl | silane Amt. (g) | Reaction Time (hr) | Product Amt. (g) | Composition of Product (%) | | | |
| | | | | | | III | IV | V | others |
| 26 | t-BuCl | 1:4 | 49.5 | 2.0 | 83.8 | 43.2 | 10.8 | 2.1 | 43.9 |
| 27 | n-BuCl | 1:4 | 49.5 | 2.0 | 95.8 | 40.8 | 8.5 | 1.3 | 49.4 |
| 28 | i-PrCl | 1:4 | 49.5 | 2.0 | 91.3 | 37.5 | 9.7 | 3.2 | 49.6 |
| 29 | $(ClCH_2)_2$ | 1:1.2 | 49.5 | 2.0 | 92.7 | — | 6.6 | 22.3 | 71.1 |

EXAMPLE 7

Reaction of Silicon with a Mixture of Dichloromethyldimethylchlorosilane and Alkyl Chloride or Hydrogen Chloride in a Fluidized Bed The reaction was carried out at 280° C. under the same condition as employed in Exp. 5 of Example 3, except that a fluidized bed reactor was employed instead of an agitating-type reaction bath. The reaction was also carried out under the same condition and by the same reactor as employed above, except that the alkyl chlorides used in Exp. 25, 26, 27 were used instead of hydrogen chloride.

402 g of Si/Cu contact mixture (I-3) prepared in Example 2 was charged in a fluidized bed reactor, and dry nitrogen gas was blown into the reactor at the rate of 200 ml/min. After increasing the temperature in the reactor up to 280° C., a 1:4 mixture of dichloromethyldimethylchlorosilane and t-butyl chloride or hydrogen chloride was introduced to the evaporator attached to the bottom of the reactor, while nitrogen was also blown therein to improve the fluidization. After the reaction for 2 hours, 55.4 g of products was collected, while 49.5 g of dichloromethyldimethylchlorosilane was used. The same reaction was carried out using different hydrogen chloride sources but same 1:4 mixing ratio. The reaction conditions for Exp. 33 were same as those for Exp. 32 except that the pressure of the reactor was raised to 3 kg/cm². The results obtained from the reactions are shown in Table 6.

TABLE 6

| | | Product Compositions of the Reaction using a fluidized bed reactor | | | | | | | | |
|---|---|---|---|---|---|---|---|---|---|---|
| Entry No. | R-Cl | silane used (g) | Reaction Time (hr) | Product Amt. (g) | Composition of Product (%) | | | | starting material | Remark |
| | | | | | III | IV | V | others | | |
| 30 | t-Bu | 49.5 | 2.0 | 53.2 | 30.8 | 12.4 | 4.5 | 20.1 | 32.2 | |
| 31 | n-Bu | 49.5 | 2.0 | 60.3 | 25.4 | 9.8 | 2.4 | 31.6 | 30.8 | |
| 32 | H | 49.5 | 2.0 | 55.4 | 33.2 | 11.5 | 3.2 | 23.7 | 28.4 | |
| 33 | H | 49.5 | 2.0 | 58.5 | 35.9 | 12.4 | 2.7 | 22.8 | 26.2 | 3 kg/cm² |

EXAMPLE 8

Reaction of Silicon with a Mixture of Dichloromethylmethyldichlorosilane and Hydrogen Chloride Si/Cu contact mixture (I-3) prepared in Example 2 was reacted with a 1:4 mixture of dichloromethylmethyldichlorosilane (55.3 g) and hydrogen chloride under the same condition as employed in Example 3. After 2 hours reaction at 280° C., 81.6 g of products was obtained. The composition of the products contained 45.7 g (56.0%) of 1,1,3,3-tetrachloro-2-(dichlorosilyl)-1,3-disilabutane (Formula III); [NMR(CDCl$_3$); δ, 5.84 (s, 2H, Si-13 H), 1.56 (s, 1H, —CH=), 1.10(s, 3H, —CH=)], 14.3 g (17.5%) of 1,1,3,3-tetrachloro-2-(trichlorosilyl)-1,3-disilabutane (Formula IV); [NMR(CdCl$_3$); δ, 5.88 (s, 1H, Si—H), 1.83 (s, 1H, —CH=), 1.13(s, 3H, —CH$_3$)], and 1.8 g (2.2%) of 1,1,3,3-pentachloro-2-(trichlorosilyl)-1,3-disilabutane (Formula V); [NMR(CDCl$_3$); δ, 2.10 (s, 1H, —CH=), 1.16 (s, 3H, —CH$_3$)]. The rest of balance was trichlorosilane (2.2%), tetrachlorosilane (0.4%), 1,1,3,3-tetrachloro-1,3-disilabutane (11.0%), 1,1,1,3,3-pentachloro-1,3-disilabutane (1.3%), and unidentified materials (9.4%).

EXAMPLE 9

Reaction of Silicon with a Mixture of Dichloromethyltrichlorosilane and Hydrogen Chloride The reaction was carried out under the same condition and by the same reactor as employed in Example 8, except that dichloromethyltrichlorosilane was used instead of dichloromethylmethyldichlorosilane (60.8 g). After 2 hours reaction at 280° C., 82.4 g of products was obtained. The composition of the products contained 1,1,1,3,3-pentachloro-2-(dichlorosilyl)-1,3-disilapropane (Formula III) 39.6 g (48.0%) [NMR(CDCl$_3$); δ, 5.87 (s, 2H, Si—H), 1.83 (s, 1H, —CH=)], 1,1,1,3,3-pentachloro-2-(trichlorosilyl)-1,3-disilapropane (Formula IV), 11.1 g (13.5%) [NMR(CDCl$_3$); δ, 5.89 (s, 1H, Si—H), 2.10 (s, 1H, —CH=)], and 1,1,1,3,3,3-hexachloro-2-(trichlorosilyl)-1,3-disilapropane (Formula VI) 2.1 g (2.6%) [NMR(CDCl$_3$); δ, 2.37 (s, 1H, —CH=)]. The by-products contained 1,1,1,3,3-pentachloro-1,3-disilapropane (13.6%), 1,1,1,3,3,3-hexachloro-1,3-disilapropane (3.3%), trichlorosilane (7.1%), tetrachlorosilane (0.9%), and unidentified materials (11.0%).

EXAMPLE 10

Reaction of Silicon with a Mixture of Dichloromethyltrimethylsilane and Hydrogen Chloride The reaction was carried out under the same condition and by the same reactor as employed in Example 8, except that dichloromethyltrimethylsilane was used instead of dichloromethyltrichlorosilane (41.6 g). After 2 hours reaction at 280° C., 72.1 g of products was obtained. The composition of the products contained 38.3 g (53.1%) of 1,1-dichloro-3,3-dimethyl-2-(dichlorosilyl)-1,3-disilabutane (Formula III); [NMR(CDCl$_3$); δ, 0.81 (s, 1H, —CH=), 0.35 (s, 9H, —CH$_3$)], 7.1 g (9.9%) of 1,1-dichloro-3,3-dimethyl-2-(trichlorosilyl)-1,3-disilabutane (Formula IV); [NMR(CDCl$_3$); δ, 5.77 (s, 1H, Si—H, 1.10 (s, 1H, —CH=), 0.39 (s, 9H, —CH$_3$)] and 0.6% of 1,1,1-trichloro-3,3-dimethyl-2-(trichlorosilyl)-1,3-disilabutane (Formula V); [NMR(CDCl$_3$); δ, 1.39 (s, 1H, —CH=), 0.43 (s, 9H, —CH$_3$)]. The by-products contained 7.5 g (10.4%) or 2,2,4-trichloro-3-(dichlorosilyl)-4-methyl-2,4-disilapentane; [NMR(CDCl$_3$); δ, 5.84 (s, 1H, Si—H), 1.22 (s, 1H, —CH=), 1.06 (s, 3H, —CH$_3$), 0.76 (s, 6H, —CH$_3$)], 1,1-dichloro-3,3-dimethyl-1,3-disilabutane (12.3%), 1,1,1-trichloro-3,3-dimethyl-1,3-disilabutane (1.0%), trichlorosilane (3.0%), tetrachlorosilane (0.3%) and unidentified materials (9.4%).

What is claims is:

1. Tris(silyl)methane represented by Formula VI:

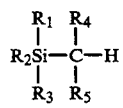

Formula VI wherein R$_1$, R$_2$, and R$_3$ are all independently methyl, or R$_1$ is methyl and both of R$_2$ and R$_3$ are chloride, or R$_1$ is chloride and both of R$_2$ and R$_3$ are methyl; and R$_4$ and R$_5$ are all SiHCl$_2$ or SiHCl$_3$, or R$_4$ is SiHCl$_2$ and R$_5$ is SiCl$_3$.

* * * * *